United States Patent [19]

Benson

[11] Patent Number: 5,755,794
[45] Date of Patent: *May 26, 1998

[54] APPARATUS FOR SIMPLIFYING TOTAL HIP ARTHROPLASTY

[75] Inventor: Gail M. Benson, Sioux Falls, S. Dak.

[73] Assignee: Bentwood Place Inc., Sioux Falls, S. Dak.

[*] Notice: The term of this patent shall not extend beyond the expiration date of Pat. No. 5,318,571.

[21] Appl. No.: 718,210

[22] Filed: Sep. 20, 1996

Related U.S. Application Data

[60] Continuation of Ser. No. 250,164, May 27, 1994, Pat. No. 5,603,717, which is a division of Ser. No. 882,938, May 14, 1992, Pat. No. 5,318,571.

[51] Int. Cl.$^6$ .......................... A61F 2/28; A61B 17/56
[52] U.S. Cl. ........................ 623/16; 606/53; 606/102
[58] Field of Search ...................... 606/102, 53, 96, 606/86, 87, 89, 54, 55, 56, 57, 58, 59, 91; 623/22

[56] References Cited

U.S. PATENT DOCUMENTS

| | | |
|---|---|---|
| 2,353,291 | 7/1944 | Blickman . |
| 2,355,585 | 8/1944 | Halstead . |
| 2,621,409 | 12/1952 | Dvorak . |
| 2,752,683 | 7/1956 | Crane . |
| 2,756,507 | 7/1956 | Martin et al. . |
| 3,002,280 | 10/1961 | Bennett, Jr. . |
| 3,392,449 | 7/1968 | Tierney . |
| 3,394,459 | 7/1968 | Grant . |
| 3,639,995 | 2/1972 | Gardner . |
| 3,643,651 | 2/1972 | Cuadros . |
| 4,279,260 | 7/1981 | Stump . |
| 4,662,365 | 5/1987 | Gotzen et al. ............ 128/92 ZW |
| 4,782,842 | 11/1988 | Fietti, Jr. ............... 128/92 ZW |
| 4,843,720 | 7/1989 | Kim . |
| 4,846,194 | 7/1989 | Sabia . |
| 4,988,349 | 1/1991 | Pennig ....................... 606/58 |
| 5,122,145 | 6/1992 | Fishbane .................... 606/102 |
| 5,148,606 | 9/1992 | Mason et al. . |
| 5,156,162 | 10/1992 | Gerhardt . |
| 5,318,571 | 6/1994 | Benson ...................... 606/102 |
| 5,423,828 | 6/1995 | Benson . |
| 5,603,717 | 2/1997 | Benson . |

FOREIGN PATENT DOCUMENTS

| | | |
|---|---|---|
| 8702883 | 5/1987 | European Pat. Off. . |
| 9412109 | 6/1994 | European Pat. Off. . |

OTHER PUBLICATIONS

J. Edeen, et al., in "Clinical Significance of Leg-Length Inequality After Total Hip Arthroplasty".

(List continued on next page.)

*Primary Examiner*—Debra S. Brittingham
*Attorney, Agent, or Firm*—Fredrikson & Byron, P.A.

[57] ABSTRACT

An apparatus for use in surgical hip replacement procedures for ensuring that the replacement hip joint components are properly sized. The acetabulum and femur are exposed, one end of a flexible measuring cable is attached to the superior eminence of the acetabulum and the cable is extended inferiorly so that it is aligned with a specific point on the femur, preferably the lesser trochanter. The selected point on the femur is marked and the scaling or marking indicator carried by the flexible cable is positioned in relation thereto. After this reference distance between the fixed points is determined, the flexible cable is moved out of the way while its end remains fixed to the acetabulum. The installation of an acetabular cup prosthesis and the femur is prepared to receive the femoral implant. After the femur is prepared, trial femoral implants are installed to determine the proper fit with the femoral canal. The selection of the proper neck length to ensure the proper resulting leg length is facilitated by extending the flexible cable attached at one end to the superior eminence of the acetabulum toward the marked position of the femur so that the marked position is aligned with the indicator fixed to the cable. The neck length of the femoral implant may be selected to match the distance between the inferior surface of the replacement acetabular cup prosthesis and the stem of the femoral implant.

4 Claims, 5 Drawing Sheets

OTHER PUBLICATIONS

Harris, W.H., "A New Approach to Total Hip Replacement Without Osteotomy of the Greater Trochanter.". *Clinical Orthopaedics and Related Research*, No. 106, Jan.–Feb. 1975, pp. 19–26.

W.H. Harris, M.D., "Revision Surgery for Failed Nonseptic Total Hip Arthroplasty," *Clinical Orthopaedics and Related Research*, 1982, 170:8–20.

W.E. Knight, M.D. ("Accurate Determination of Leg Lengths During Total Hip Replacement," *Clinical Orthopaedics and Related Research*, 1977, 123:27–28.

Love, B.R.T., and Wright, J., "Leg Length Discrepancy After Total Hip Replacement," *Journal Bone Joint Surgery*, vol. 65B, Jan. 1983, p. 103.

N.M.J. McGee, F.R.C.S., et al., "A Simple Method of Obtaining Equal Leg Length in Total Hip Arthroplasty," *Clinical Orthopaedics and Related Research*, 1985, 194:269–270.

"Arthroplasty of Hip" p. 493, pp. 540–542.

Petty, William, "Lower Extremity Replacement: The Hip; Total Hip Arthroplasty: Complications," *Total Joint. Replacement*, W.B. Saunders Company, 1991, pp. 304–305.

Steinberg, Marvin E., "Reconstruction Surgery of the Adult Hip–Cemented Total Hip Replacement: Operative Techniques; Limb Length Equalization," *The Hip and Its Disorders*, W.B. Saunders Company, 1991, pp. 963–966.

Harris, W.H., "Total Hip Replacement for Failed Endoprostheses and Cup Arthroplasty: Technical Considerations," *AAOS Instructional Course Lectures*, vol. 23, St. Louis, C.V. Mosby, 1974, pp. 154–163.

Turula, Kaj B., et al; "Leg Length Inequality After Total Hip Arthroplasty," *Clinical Orthopaedics and Related Research*, No. 202, Jan. 1988, pp. 163–168.

Williamson, John A., et al; "Limb Length Discrepancy and Related Problems Following Total Hip Joint Replacement," *Clinical Orthopaedics and Related Research*, No. 134, Jul.–Aug. 1978, pp. 135–138.

Woolson, Steven T.; "Leg Length Equalization During Total Hip Replacement," *Orthopedics*, vol. 13, No. 1, Jan. 1990, pp. 17–21.

Love, B.R.T., and Wright, J., "Leg Length Discrepancy After Total Hip Joint Replacement," *Journal Bone Joint Surgery*, vol. 65B, Jan. 1983, p. 103.

N.M.J. McGee, F.R.C.S., et al., "A Simple Method of Obtaining Equal Leg Length in Total Hip Arthroplasty," *Clinical Orthopaedics and Related Research*, 1985, 194:269–270.

"Arthroplasty of Hip" p. 493, pp. 540–542.

APPARATUS FOR SIMPLIFYING TOTAL HIP ARTHROPLASTY

CROSS-REFERENCE TO RELATED APPLICATIONS

This is a continuation of application Ser. No. 08/250,164, filed May 27, 1994, now U.S. Pat. No. 5,603,717, which was a divisional of Ser. No. 07/882,938 filed May 14, 1992 (issed as U.S. Pat. No. 5,318,571).

BACKGROUND OF THE INVENTION

1. Field of the Invention

The present invention relates to a method and apparatus for facilitating the total hip arthroplasty procedure in which both an acetabular cup prosthesis and a femoral implant prosthesis are installed or in a partial hip arthroplasty where one of the components of an earlier arthroplasty are replaced and particularly, to a method and apparatus for assuring that the resulting leg length of the patient is optimized.

2. Description of the Prior Art

Total and replacement arthroplasty procedures employing artificial acetabular cup prostheses and femoral implants have been done for a great many years. The installation of a replacement hip joint prosthesis involves surgically exposing and dislocating the joint, cutting away the head and neck and a portion of the greater trochanter in a femoral neck resection, and reaming the femoral canal to accept the metallic stem of the femoral implant. Femoral implants are available in a variety of lengths and cross-section to fit the shape of the reamed-out femoral canal and are also provided with an angularly disposed femoral neck and spherical head that extend at an angle to the stem to orient the replacement head in the acetabular cup prosthesis. The acetabular cup prosthesis is itself installed in the patient's reamed-out acetabulum. After both components are installed, the spherical head is inserted into the cup and the muscles and tendons that were separated or severed in the surgical exposure are reattached to hold the leg in place.

Numerous articles have been published describing and illustrating total hip arthroplasty procedures employing a wide variety of total hip joint prostheses. For example, the publication entitled "Total Hip Arthroplasty Using a Universal Joint Device," by Raymond G. Tronzo, M.D., published in 1970 by Richards Manufacturing Company, 1450 Brooks Road, Memphis, Tenn. 38116, describes such a procedure employing the products of the Richards Manufacturing Company. A further brochure entitled "PERFECTA Femoral Prostheses With T-MATRIX Acetabular Options—Surgical Protocol," published in 1990 by Orthomet, Inc., 6301 Cecilia Circle, Minneapolis, Minn. 55439, describes and illustrates the surgical procedure employed in installing Orthomet products. Other manufacturers publish similar instruction manuals or protocols for their products.

A common problem that arises in completing the total hip arthroplasty procedure involves the selection of the appropriate length neck of the femoral implant so that after the procedure is completed, the patient enjoys a normal or enhanced leg length. If only one of the patient's legs is operated on, it is naturally desirable to ensure that the patient's legs are of approximately the same length after recovery from the surgery. Often, due to deterioration in the hip joint, the leg may initially be shorter than desired and the replacement surgery should include restoration of nearly equal leg length. When both hip joints are placed, it may be desirable to equalize and lengthen both legs. In any case, a common problem that is encountered involves the failure of the prosthesis to restore the desired leg length, causing the patient to limp and contributing to a low-back pain and aseptic loosening of the cement used to fix the components of the hip joint, as reported by K. B. Turula, M.D., et. al., in "Leg Length Inequality After Total Hip Arthroplasty," *Clinical Orthopaedics and Related Research*, 1986; 202:163-168.

In this regard, published reports in the literature indicate that the precise desired length of the leg is obtained perhaps no more than about one-fourth of the time. Approximately one-half of the time, the leg can vary from a desired length by up to one half inch. The remaining one-fourth of the time, the leg is too short or too long by substantially greater lengths ranging up to an inch or two. Although patients can tolerate length differences of ¼-inch or thereabouts, differences in length of ½ inch or more are immediately detected by patients and often times are intolerable. When this occurs, it is necessary to reoperate and change the length or provide the patients with heel lifts to equalize leg length and restore proper gait.

The differences in leg length arise from the difference in sizes of the femoral implants, the depth of insertion of the acetabular cup, and the length of the reduced femoral neck. To change the length of a leg, the surgeon simply changes the length of the femoral neck that is used. Once the acetabular cup is in place, it is rarely changed.

A variety of methods have been used to estimate the length of the leg upon implanting a new femoral implant and acetabular cup. Most of the time, a surgeon will attempt to duplicate it with the femoral implant, the size not varying greatly from the size of the proximal femoral portion that is removed.

Some methods have involved measuring the distance from the palpable iliac crest near the waist line to the greater trochanter on the outside of the proximal femur, both of these markers are quite distance from the true hip joint and only indirectly attempt to measure length.

Other methods described in the literature measure the distance from an anchor installed percutaneously above the superior acetabulum to a marker on the exposed greater trochanter. See, for example, S. T. Woolson, M.D., et. al., "A Method of Interoperative Limb Length Measurement in Total Hip Arthroplasty," *Clinical Orthopaedics and Related Research*, 1984, 194:207-210; W. H. Harris, M.D., "Revision Surgery for Failed Nonseptic Total Hip Arthroplasty," *Clinical Orthopaedics and Related Research*, 1975, 106:19-26; and N. M. J. McGee, F.R.C.S., et. al., "A Single Method of Obtaining Equal Leg Length in Total Hip Arthroplasty," *Clinical Orthopaedics and Related Research*, 1985, 194:269-270. In an article by W. E. Knight, M.D. ("Accurate Determination of Leg Lengths During Total Hip Replacement," *Clinical Orthopaedics and Related Research*, 1977, 123:27-28), a tool is described for measuring the distance between bone screws placed in the exposed ilium about two inches above the margin of the acetabulum and in the greater trochanter of the femur in line with the iliac screw in the coronal plane. The tool is positioned laterally to the pins and the measurement is made parallel to the femur, which is not necessarily parallel to the weight-bearing axis.

These methods are flawed as they measure two dimensions, length (vertical dimension) plus lateralization (horizontal translation of the femur). The hip and leg position must be virtually identical when pre-op and post-op measurements are made to insure predictable results. In practice, the horizontal offset and leg position are difficult to replicate. A better surgical procedure for obtaining exact leg length is much to be desired.

SUMMARY OF THE INVENTION

It is therefore an object of the present invention to decrease the occurrences of unbalanced leg lengths resulting from implantation of hip prostheses.

It is a further object of the invention to provide a method and apparatus for accurately measuring the vertical distance traversing the acetabulum and femur in the direction of the weight-bearing axis to decrease the occurrence of leg length imbalance.

The invention relates in one aspect to a surgical hip replacement procedure that is particularly adapted for exactly controlling in a predetermined manner the length of the leg that will result. In another aspect, the invention relates to an apparatus, which may be in kit form, for performing the surgical procedure.

The procedure involves:

preoperatively measuring the patient's legs and noting any disparity in length;

surgically exposing the superior portion of the femur and the acetabular region of the iliac bone;

marking or forming an attachment to a fixed position on the iliac bone, e.g., the superior eminence of the acetabulum;

marking or forming an attachment to the femur approximately at the level of the lesser trochanter such that a straight line drawn between said marks or attachments is approximately parallel to and closely spaced from the weight supporting axis of the femur (that is, a line that connects that connects the center of rotation of the femoral ball and that passes through the center of the knee).

noting the distance between said marks or attachments when the femur is held in a normal extended position;

performing the surgical task of implanting an acetabular cup prosthesis and a trial proximal femoral prosthesis having a head received in the cup;

noting the distance between the marks or attachments to determine whether the distance between them has increased, decreased or remained the same; and adjusting or replacing one or both of said prostheses if needed to provide the desired distance between said attachments, the distance correcting any noted disparity in initial leg length.

In another aspect, the invention involves a calibration apparatus comprising a first attachment attachable to the superior eminence of the acetabulum, a second attachment attachable to the femur at approximately the level of the lesser trochanter, and a cable having one end adapted to be attached to one of said attachments and with its other end extending toward the other attachment, the cable including means for noting on the cable the point representing the position of the other of the two attachments.

In a first preferred embodiment, the cable has a free end that is attachable to one of said attachments, the cable including scale means carried by and movable longitudinally of the cable, the scale means including indicia that can be positioned at the location of said other attachment, and fixation means for fixing the scale at a desired position along the length of said cable. Most preferably, the cable has at its other end means for attaching it to other objects, such as a surgical drape, to hold the cable out of the way during the surgical procedure.

Because the distance between the superior eminence of the acetabulum and the position of the lesser trochanter of the femur is very close to being parallel to the weight supporting axis of the leg, changes in distance along the weight supporting axis of the leg are reflected directly in changes in distance along the cable. If the cable indicates that the distance between the two attachments has been reduced by ½-inch, the length of the leg will have been reduced by ½-inch.

BRIEF DESCRIPTION OF THE DRAWINGS

These and other objects and advantages and features of the present invention will become apparent from the following detailed description of the preferred embodiments thereof in conjunction with the drawings in which.

DESCRIPTION OF THE PREFERRED EMBODIMENTS

Figure 1:
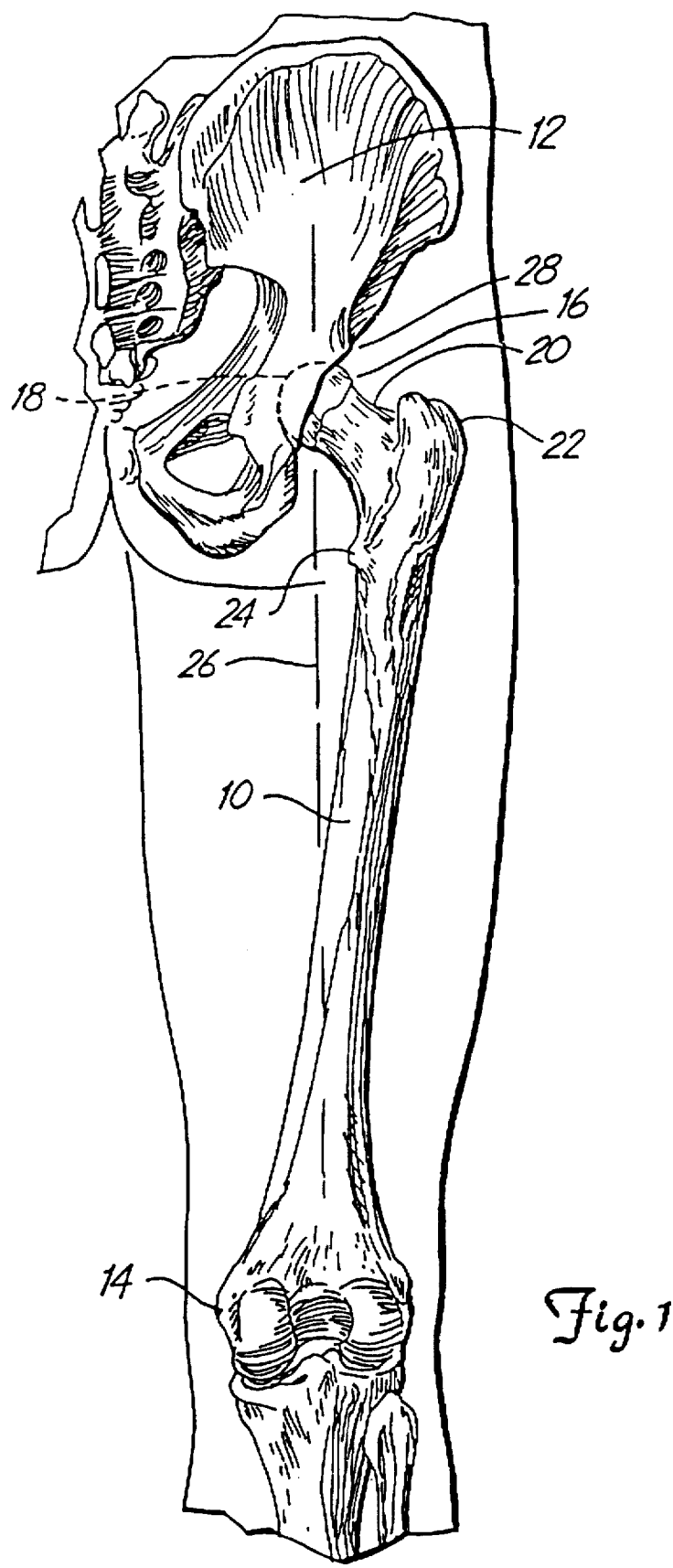
FIG. 1 is a posterior view of the right pelvic girdle and a portion of the right leg bones.

Turning now to the drawings and first to FIG. 1, it illustrates a posterior view of the right pelvic girdle and a portion of the right leg showing the normal alignment of a human hip joint in relation to the knee joint. The femur 10, or thigh bone, articulates at its proximal end with the iliac bone 12. Its distal end articulates with the tibia at the knee joint 14. The shaft of the femur bows medially so that it approaches the femur of the opposite thigh. As a result of this convergence, the knee joints are brought together to the body's line of gravity or weight supporting axis.

The proximal end of the femur 10 comprises the rounded head 16 that articulates with the acetabulum 18 of the iliac bone 12. The neck 20 of the femur 10 is a constricted region distal to the head 16. A fairly common fracture in the elderly occurs at the neck 20. Apparently the neck 20 becomes so weak that it fails to support the body. The greater trochanter 22 and lesser trochanter 24 are projections on the femur 10 that serve as points of attachment for some of the thigh and buttock muscles. Between the trochanters on the anterior surface is a narrow introchanteric line. Between the trochanters on the posterior surface is an intertrochanteric crest. The shaft of the femur contains a rough vertical ridge on its posterior surface called the linea aspera. This ridge serves for the attachment of several thigh muscles. The distal end of the femur is expanded and includes the medial condyle and the lateral condyle. These articulate with the tibia and (with attendant ligaments, etc.) from the knee joint 14.

The weight of the body is borne by the normal pelvic girdle and lower extremities in conjunction with the associated muscles and ligaments in a weight supporting axis extending generally through the superior aspect of the acetabulum 18 inferiorly alongside the femur and through the center of the knee joint 14 generally as illustrated by broken line 26 in FIG. 1. The weight supporting axis 26 passes through or adjacent to a line draw in between the superior eminence 28 of the acetabulum and the lesser trochanter 24.

Through disease processes or injury, the hip joint may become less mobile, painful or totally unusable, requiring surgical intervention and a total hip arthroplasty employing a hip joint prosthesis of the type described in the above-referenced publications. A wide variety of prostheses are available from several manufacturers, the prostheses typically including a metal acetabular cup for surgical replacement of the natural acetabulum 18, a high density polyethylene cup liner positioned within the cup prosthesis and a femoral implant comprising a femoral stem and a femoral ball-shaped head of the type illustrated in FIG. 2.

Figure 2:
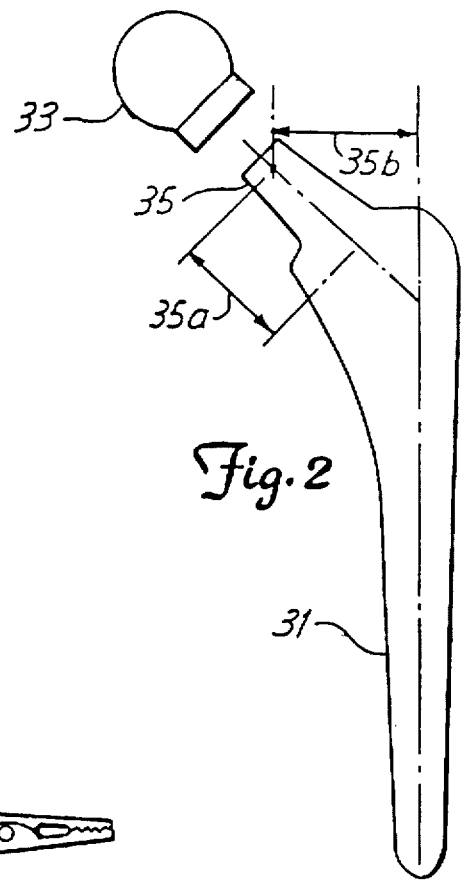
FIG. 2 is an illustration of a femoral implant of a type employing a separate head adapted to fit in an acetabular cup of a total hip joint replacement prosthesis.

Turning now to FIG. 2, it illustrates a typical femoral implant stem 31 and femoral implant head 33 which are attached together to form the femoral implant 29. The femoral stem 31 is available in a number of cross-section shapes, sizes and lengths having varying exterior contours, neck offsets and neck lengths. The femoral implant head 33 is usually a highly polished, spherical metal ball provided in a number of available diameters and neck lengths and provided with a Morse taper female receptacle for receiving the Morse tapered neck 35 of a stem 31. In practice, manufacturers of total hip prostheses provide a selection of different neck length femoral implant stems 31 and femoral implant heads 33. Thus, it is possible to customize the overall neck length as necessary to replicate the proper leg length for the individual patient.

As described above, upon completion of the operative procedure, it has often been found that the overall leg length is incorrect, requiring a reoperation, usually involving replacement of one or both of the components of the femoral implant to lengthen the replacement neck that substitutes for the neck 20 of the original femur illustrated in FIG. 1. I have found that the operative procedure may be simplified and the need to reoperate substantially eliminated by providing a calibrated measurement between respective fixed points of the iliac bone and femur along the weight supporting axis 26 prior to dislocating the femoral head 16 from the acetabulum 18 and employing the calibrated distance, adjusted positively or negatively if the leg operated on is shorter or longer than the patient's other leg in positioning the resected femur in relation to the acetabular cup prosthesis for sizing the length of the neck of the femoral stem of the femoral implant.

Figure 3:
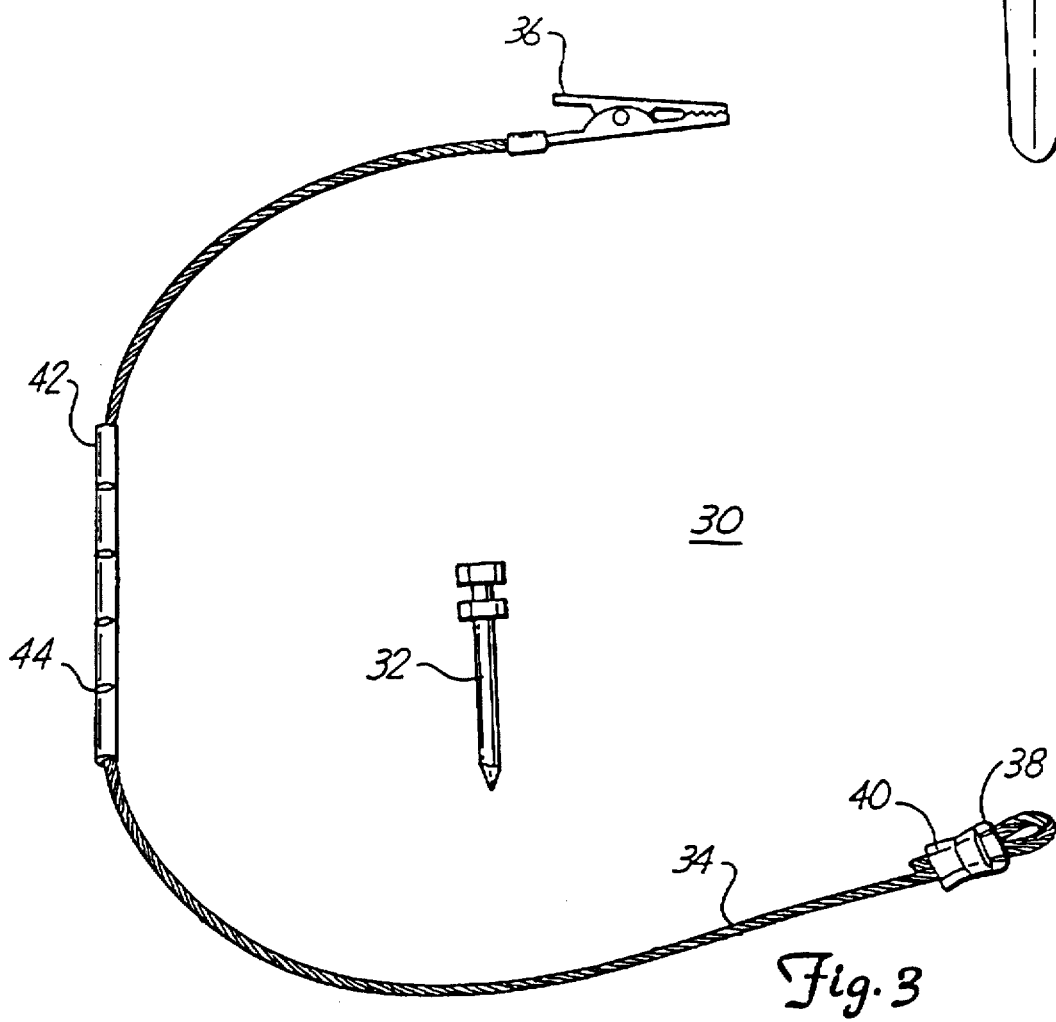
FIG. 3 is an illustration of a first embodiment of the calibration apparatus employed in the practice of the method of the present invention.
Figure 4:
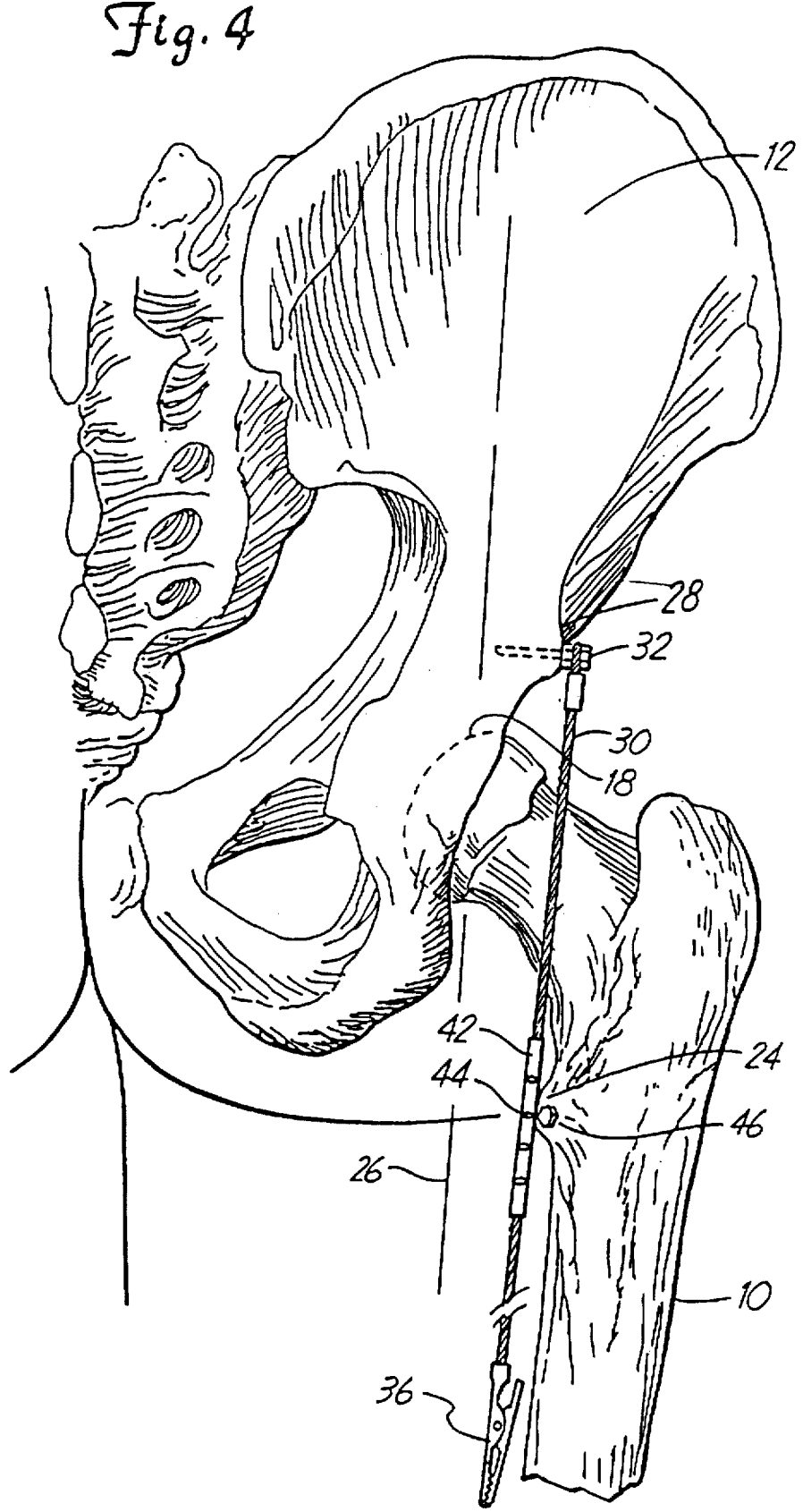
FIG. 4 is an illustration of the use of the calibration apparatus of FIG. 3 in initially measuring the distance between two points on the iliac bone and the femur in a posterior surgical approach.
Figure 5:
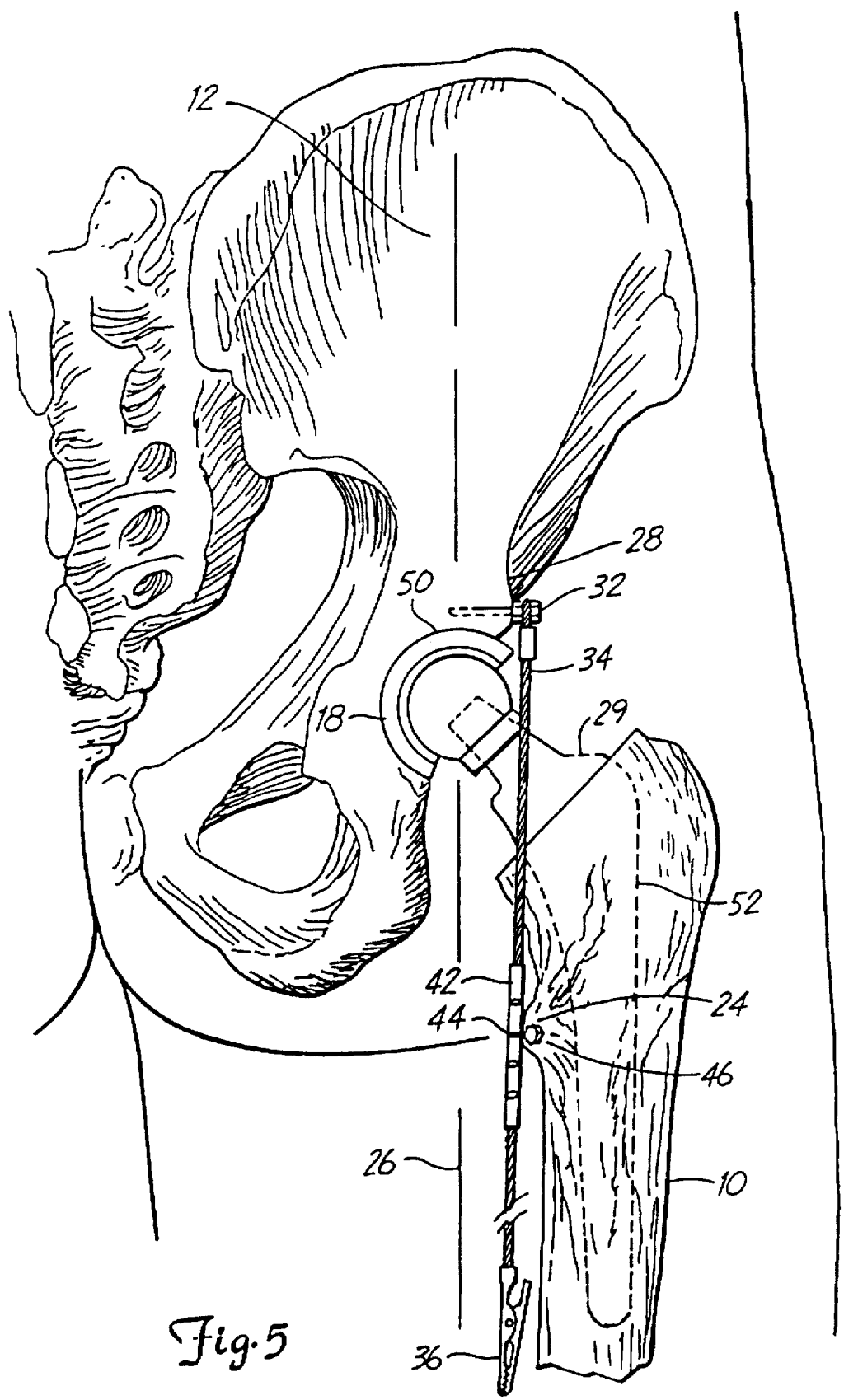
FIG. 5 is an illustration of the use of the calibration apparatus of FIG. 3 in selecting the appropriately sized femoral implant in accordance with the method of the present invention practiced in a posterior surgical approach.

To this end, FIG. 3 illustrates a calibration apparatus 30 comprising length of cable 34 and a bone nail 32 that are used as illustrated in FIGS. 4 and 5 to select a properly sized femoral stem 31 and head 33 during the procedure and avoid reoperation. The calibration apparatus depicted in FIG. 3 comprises a length of stranded wire cable 34 extending between an alligator clip 36 and a loop 38 formed by bending the cable 34 back against itself and crimping a crimp tube 40 around both to form a loop. The loop 38 is formed after the bone nail 32 is fixed in the region of the superior eminence 28 of acetabulum 18 as shown in FIG. 4.

The alligator clip 36 is provided so that the free end of the cable 34 may be attached to a surgical drape to hold the apparatus 30 out of the surgical field when it is not used in the manner depicted in FIGS. 4 and 5.

The calibration apparatus 30 depicted in FIGS. 3-5 also includes a slideable tube 42 having four calibration marks 44 spaced apart about one centimeter in the outer surface of the tube 42. The calibration tube 42 may be slid back and forth on the length of stranded wire cable 34 so that one of the marks 44 is aligned with a mark or attachment, e.g., another bone nail 32, made on the femur 10 and crimped in place by a crimping tool.

Turing now to FIG. 4, it illustrates the placement of the calibration apparatus 30 to effect a calibrated measurement of distance along the weight supporting axis 26 between the femur 10 and the iliac bone 12 before the head 16 is dislocated from the acetabulum 18. It will be understood that for the sake of simplicity, the operating field, including the incision and the separation of the muscles and ligaments, are not illustrated in FIGS. 4 and 5. Assuming that those operative steps have been taken and the proximal end of the femur 10 and the portion of the iliac bone 12 surrounding the acetabulum 18 are exposed, the surgical nail 32 is driven into the region of the superior eminence 28 of the acetabulum 18 about 2 centimeters above the acetabular rim in the 11 o'clock position after the loop 38 in the cable 34 has been mechanically attached to the head of the nail 32. Thereafter, the cable 34 is extended in the direction of the weight supporting axis 26 bringing it alongside the lesser trochanter 24. Then, as shown in FIG. 4, the slideable calibration tube 42 is moved along the length of cable 34 until one of its indicia 44 is aligned with a mark 46 made on the lesser trochanter 24. The mark 46 may in fact be a further surgical nail driven into the bony protruberance of the lesser trochanter 24 since it is difficult to otherwise mark the bone.

After the indicia 44 and nail 46 are aligned, the tube 42 is crimped tightly against the stranded wire cable 34 so that it cannot be moved or dislodged. The selected indicia 44 is noted in the surgical record and the cable 34 is pivoted superiorly out of the operating field. The alligator clip 36 is attached to a surgical drape covering the patient's torso in order to keep the apparatus 30 out of the surgical field to allow the surgeon to dislocate the head 16 from the acetabulum 18 and proceed with the resection of the femur and the surgical placement of the acetabular cup prosthesis and the reaming of the femoral canal to accept the trial femoral components in the manner described in the above-incorporated publications.

Turning now to FIG. 5, it illustrates the placement of an artificial acetabular cup prosthesis 50 in the location of the acetabulum 18 and the insertion of a trial femoral implant 29 comprising the femoral implant stem 31 and femoral implant head 33 in relation to the acetabular cup prosthesis 50 and the femoral canal 52 outlined in the resected femur 10. Once the acetabular cup prosthesis 50 is surgically implanted and the femoral canal 52 is reamed out, a trial femoral implant 29 is inserted as shown in FIG. 5 to test the fit and the articulation of the leg. As described above, the failure to select the proper neck length of the femoral implant 29 may cause the patient to suffer from an imbalance in the resulting leg length.

In accordance with the method of my invention, the calibration apparatus 30 is employed in the trial fitting stage to ensure that the selected neck length results in the desired leg length. As illustrated in FIG. 5, once a trial femoral implant 29 is in place, the stranded wire cable 34 is extended in the direction of the weight supporting axis 26 to determine whether or not the calibration indicia 44 previously aligned to the mark or nail 46 is again aligned. If the measurement indicates that the actual position is superior or inferior to the noted calibration indicia 44, then the trial femoral implant 29 is withdrawn and/or longer or shorter necked components are substituted. The process is repeated until the calibration indicia is aligned as closely as possible to the femoral mark or nail.

In the event that it was determined prior to beginning the surgical procedure that the patient's leg needed to be lengthened or shortened, then the lengthened or shortened amount may be taken into account when the calibration mark 44 is noted as described and illustrated in respect to FIG. 4.

After the properly sized components are installed, the surgical nail 32 and 46 (if used) as well as the cable 34 are removed and the incision is closed in the normal manner. By use of the inventive tool and procedure, the incidence of reoperation required to correct for leg length errors is virtually eliminated.

Figure 6:
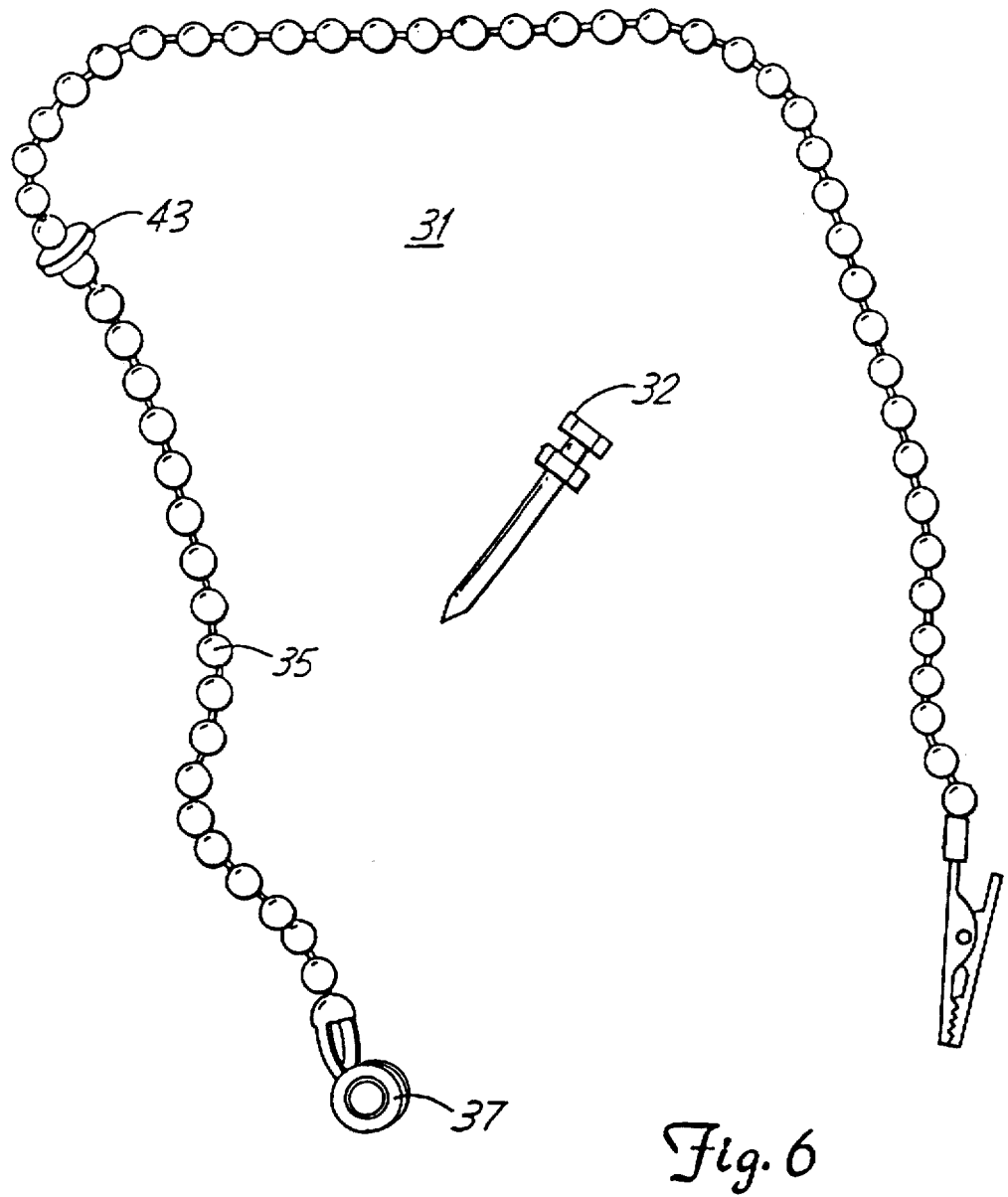
FIG. 6 is an illustration of an alternative calibration apparatus employed in the practice of the method of the present invention.

Turning now to FIG. 6, it illustrates an alternate embodiment of the calibration tool 30 employing the bone nail 32 and a length of ball or key chain 35 having an eyelet loop 37 on one end of the length of chain 35. In use, the eyelet loop 37 is attached to the head of the bone nail 32 which is nailed into the iliac bone 12 in the region of the superior eminence 28 of the acetabulum 18 as described in conjunction with FIG. 4. The chain 35 is stretched inferiorly in the direction of the weight supporting axis 26 alongside the lesser trochanter 24 and a metal clip 43 is crimped between adjacent balls of the ball chain 35 at the point where it aligns with the mark or nail 46. Thereafter, the chain is moved out of the surgical field and clipped at its free end to the surgical drape on the patient's torso. The tool 31 is used in conjunction with the sizing of the femoral implant components in the same fashion as is described in respect to FIG. 5 and thereafter removed.

The procedure described above involves a posterior surgical exposure of the hip joint. In practice, the procedure may be used in an anterior surgical approach. In that case, the mark or nail 46 may be made or inserted in the anterior-medial cortex at the level of the lesser trochanter. The nail 32 is advantageously inserted about 2 centimeters above the acetabular rim in the one o'clock position. The cable 34 or chain 35 is extended therebetween as described above but along the anterior side of the neck of the femur and in line with the weight-bearing axis. Selection of the anterior or the posterior approach is left to the discretion of the surgeon.

The invention has been described in detail with particular reference to the preferred embodiments thereof, but it will be understood that variations and modifications can be effected within the spirit and scope of the invention.

What is claimed is:

1. An apparatus for use in orthopedic and reconstructive surgery conducted on a patient, the apparatus being useful for making skeletal distance measurements between first and second reference points on first and second bones making up a joint, comprising:

(a) a flexible extendable measuring device having first and second ends;

(b) attachment means for attaching the first end of the measuring device to skeletal bone of the patient at the first reference point such that the measuring device may be extended in a desired direction alongside the second reference point to effect a desired skeletal distance measurement therebetween and said second end of the measuring device may be repositioned to other positions out of surgical field when not used for such measurement, and (c) distance indicating means associated with the device for measuring a first distance from the first reference point to the second reference point while the first and second bones are in a first position afforded by the bone joint, whereby the measuring device may be moved to the other positions during reconstructive surgery conducted on the patient.

2. The apparatus of claim 1 wherein the distance indicating means comprise calibrations along the length of the device.

3. The apparatus of claim 2 wherein the calibrations are provided by one or more tubular, slidable members fitting over and around the measuring device and slidable between the first and second ends thereof, the tubular members each having at least one calibration indicia on its surface and being fabricated of a material capable of being crimped against the device in order to mark the measured distance therealong.

4. The apparatus of claim 1 further comprising:

attaching clip means coupled to the second end of the measuring device for allowing the second end of the device to be attached out of and away from the operating field.

* * * * *

UNITED STATES PATENT AND TRADEMARK OFFICE
CERTIFICATE OF CORRECTION

PATENT NO. : 5,755,794

DATED : May 26, 1998

INVENTOR(S) : Benson

It is certified that error appears in the above-identified patent and that said Letters Patent is hereby corrected as shown below: On title page, item [54] and col. 1, line 1,
In the title, kindly delete "TOTAL HIP" and insert therefore – JOINT –.

Signed and Sealed this

Seventh Day of September, 1999

Attest:

Q. TODD DICKINSON

Attesting Officer

Acting Commissioner of Patents and Trademarks